US008647640B2

(12) United States Patent
Cowart

(10) Patent No.: US 8,647,640 B2
(45) Date of Patent: Feb. 11, 2014

(54) VACCINE COMPOSITIONS AND METHODS OF USE TO PROTECT AGAINST INFECTIOUS DISEASE

(76) Inventor: Richard E. Cowart, Dubuque, IA (US)

(*) Notice: Subject to any disclaimer, the term of this patent is extended or adjusted under 35 U.S.C. 154(b) by 106 days.

(21) Appl. No.: 12/821,825

(22) Filed: Jun. 23, 2010

(65) Prior Publication Data

US 2010/0330124 A1 Dec. 30, 2010

Related U.S. Application Data

(60) Provisional application No. 61/219,908, filed on Jun. 24, 2009.

(51) Int. Cl.
*A61K 39/02* (2006.01)

(52) U.S. Cl.
USPC .................. 424/243.1; 424/234.1; 424/258.1; 424/260.1; 424/261.1; 530/350

(58) Field of Classification Search
None
See application file for complete search history.

(56) References Cited

U.S. PATENT DOCUMENTS

| | | | | |
|---|---|---|---|---|
| 4,264,588 | A * | 4/1981 | Orcutt .......................... | 424/239.1 |
| 4,755,381 | A * | 7/1988 | Cryz ........................... | 424/259.1 |
| 4,957,739 | A * | 9/1990 | Berget et al. ............... | 424/190.1 |
| 5,352,448 | A * | 10/1994 | Bowersock et al. ......... | 424/438 |
| 5,378,615 | A * | 1/1995 | Shewen et al. ............... | 435/71.3 |
| 5,391,715 | A * | 2/1995 | Capiau et al. ................ | 530/396 |
| 6,013,463 | A * | 1/2000 | Cover et al. .................. | 435/7.92 |
| 6,248,570 | B1 * | 6/2001 | Michon et al. ................ | 435/101 |
| 6,559,176 | B1 * | 5/2003 | Bassler et al. ................ | 514/408 |
| 2002/0119161 | A1 * | 8/2002 | Suehara et al. ............ | 424/185.1 |
| 2002/0123077 | A1 * | 9/2002 | O'Toole et al. ................ | 435/7.2 |
| 2003/0133941 | A1 * | 7/2003 | Suehara et al. ............ | 424/185.1 |
| 2007/0041997 | A1 * | 2/2007 | Finlay et al. ............... | 424/200.1 |

FOREIGN PATENT DOCUMENTS

| | | | |
|---|---|---|---|
| EP | 2 175 017 | 4/2010 | |
| WO | 99/45136 | * 9/1999 | ............... C12Q 1/02 |
| WO | 02/053181 A1 | 7/2002 | |
| WO | 2008/025171 | * 3/2008 | |
| WO | 2009/005040 A1 | 1/2009 | |
| WO | 2009/038756 A2 | 3/2009 | |

OTHER PUBLICATIONS

Ellis, Ronald W, Ph.D, Chapter 29, pp. 568-575, 1988, Vaccines.*
Boslego, John W et al, Gonorrhea Vaccines, Chapter 17, pp. 211-223, Vaccines and Immunotherapy, 1991.*

(Continued)

*Primary Examiner* — Albert Navarro
*Assistant Examiner* — Ginny Portner
(74) *Attorney, Agent, or Firm* — Quarles & Brady LLP

(57) ABSTRACT

The present invention provides a novel immunogenic composition, vaccine and methods for making and using the immunogenic composition and vaccine. The immunogenic composition is capable of providing an immune response and/or a protective immunity into subjects, preferably mammals, against microorganism-associated disease. The immunogenic composition includes one or more extracellular proteins isolated from a microorganism capable of providing an immune response and/or a protective immunity into subjects against microorganism-associated disease. The isolated extracellular proteins range in molecular weight from about 10,000 Da to about 220,000 Da. Suitable microorganisms may include members of the genus *Salmonella, Listeria, Pseudomonas, Staphylococcus*, and *Vibrio*. Kits are also encompassed for detection, diagnosis and prevention of microorganism-associated disease.

20 Claims, 4 Drawing Sheets

(56) References Cited

OTHER PUBLICATIONS

Dziva, F et al, FEMS Microbiology Letters, 2007, pp. 1-7, EspP, a Type V-secreted serine protease of enterohaemorrhagic *Escherichia coli* O157:H7, influences intestingal colonization of calves and adherence of bovine primary intestinal epithelial cells.*

Gildemeister, Otto S et al, Glycoconjugate Journal, 1994, vol. 11, pp. 518-526, Chitovibrin: a chitin-binding lectin from *Vibrio parahemolyticus*.*

Marquart, Mary E. et al, Invest. Ophthalmol Vis. Sci., 2005, vol. 46, pp. 3761-3768, Identification of a Novel Secreted Portease from *Pseudomonas aeruginosa* that causes cornela erosions.*

Rahman et al, Vet Microbiology, Apr. 1994, vol. 39(3-4), pp. 245-254, Purification and characterization of enterotoxic moiety present in cell-free culture supernatant of *Salmonella typhimurium*.*

Sawa, Teiji et al, Nature Medicine, 1999, vol. 5, No. 4, pp. 392-398, Active and Passive immunization with the Pseudomonas V antigen protects against type III intoxication and lung injury.*

Nuriddinova N R et al: "*Pseudomonas aeruginosa* vaccine on the basis of antigens isolated from the supernatant of culture media K-4", Database Medline [Online] 1-15, US National Library of Medicine (NLM), Bethesda, MD, US; (2002), XP002601442, Database accession No. NLM12449697.

Doring et al: "Vaccines and immunotherapy against *Pseudomonas aeruginosa*", Vaccine, Elsevier Ltd, GB LNKDDOI: 10.1016/J.Vaccine.2007.12.007, vol. 26, No. 8, (2007), pp. 1011-1024, XP022473369 ISSN: 0264-410X.

International Search Report and Written Opinion mailed Dec. 14, 2010 (International Patent Application No. PCT/US2010/039697, filed Jun. 23, 2010).

* cited by examiner

Immunogenic Extracellular Protein Band Analysis

|        | Experimental Lane (1) | Standard Lane (2) |
|--------|-----------------------|-------------------|
| Band # | MW (d)                | MW (d)            |
| 1      | 114318.2              | 170000            |
| 2      | 70853.9               | 135000            |
| 3      | 66651.7               | 100000            |
| 4      | 62831.5               | 72000             |
| 5      | 59584.3               | 55000             |
| 6      | 54861.1               | 40000             |
| 7      | 52916.7               | 30000             |
| 8      | 47777.8               | 24000             |
| 9      | 42638.9               | 17000             |
| 10     | 39875.0               |                   |
| 11     | 37375.0               |                   |
| 12     | 35250.0               |                   |
| 13     | 28963.0               |                   |
| 14     | 26000.0               |                   |
| 15     | 20421.1               |                   |
| 16     | 18789.5               |                   |

FIG. 1B

VACCINE COMPOSITIONS AND METHODS OF USE TO PROTECT AGAINST INFECTIOUS DISEASE

CROSS-REFERENCE TO RELATED APPLICATIONS

This application claims priority to U.S. Provisional Application No. 61/219,908 filed Jun. 24, 2009, the entirety of which is incorporated by reference herein for all purposes.

STATEMENT REGARDING FEDERALLY SPONSORED RESEARCH OR DEVELOPMENT

Not applicable.

BACKGROUND OF THE INVENTION

Prokaryotes are classified into two domains called Bacteria and Archaea, the latter of which are referred to as extremophiles. The invention described herein does not encompass Archaea. Bacteria are prokaryotes that consist of a cell membrane bound by a cell wall. Exceptions are bacteria in the genera *Mycoplasma, Chlamydia,* and *Ureaplasma,* all of which lack cell walls.

With the exception of those lacking cell walls, bacteria can be divided into two large groups based on the chemical and physical properties of their cell walls by Gram staining (Madigan, et al. *Brock: Biology of Microorganisms.* 12$^{th}$ ed. 2009, Pearson/Benjamin Cummings. pp. 27-28, 77-86). Gram-positive bacteria have a thick mesh-like cell wall made of peptidoglycan (50%-90% of cell wall), which stains purple when subjected to Gram-staining, while Gram-negative bacteria have a thinner layer containing less peptidoglycan (10% of cell wall), which stains pink. Gram-negative bacteria also have an additional outer membrane, which contains lipopolysaccharide (LPS). Lipopolysaccharides, which are endotoxins and are very toxic, elicit a strong immunogenic response in animals. Endotoxins trigger humoral enzymatic mechanisms involving the complement, clotting cascade, fibrinolytic, and kinin pathways and can cause morbidity associated with Gram-negative sepsis. Numerous pathogens are members of the domain Bacteria.

Bacterial Pathogens and Pathogenesis

In order for a pathogen to infect a host, the microorganism must first gain entrance into the host. Entrance may occur via inhalation, ingestion, or a break in the skin's integrity, to name but a few. After entrance, the microorganism must adhere to its host tissue. Adherence is often specific and the host can employ mechanisms to avoid adherence, such as epithelial and mucosal sloughing. Once adhered, the microorganism must colonize its host (i.e., grow on the adherence surface). Following colonization, pathogenic microorganisms initiate a process of invasion in which microbes grow within their hosts tissues. It is typically in this stage of invasion that pathogens cause symptoms of disease, as discussed herein.

Pathogenic bacteria are able to cause disease because they possess certain structural, biochemical, or genetic traits that render them virulent. The sum of the characteristics that allow a given bacterium to produce disease are the pathogen's determinants of virulence. Some pathogens may rely on a single determinant of virulence, such as a toxin, to cause damage to their host, which is described in more detail below. Other pathogens, such as *Staphylococcus aureus, Streptococcus pyogenes* and *Pseudomonas aeruginosa,* maintain a large repertoire of virulence determinants and, consequently, are able to produce a wider range of diseases that affect different tissues in their host.

A limited number of extracellular proteins and enzymes that are also virulence factors have been characterized, for example:

1. Diptheria toxin. *Corynebacterium diphtheriae,* the causative agent of diphtheria, initially infects animals via the respiratory mucosa. Upon infection, *C. diphtheriae* quickly consumes its host's local supply of iron, which is a co-repressor of the DT gene (Holmes (2000) *J. Infec. Diseases* 181: S156-S157). In response to a low-iron microenvironment, *C. diphtheria* secretes a 62 kD extracellular protein known as diphtheria toxin (Schmidt et al. (1991) *Infection and Immunity.* 59: 1899-1904). This toxin, released into the blood steam, causes the progressive deterioration of myelin sheaths in the central and peripheral nervous system leading to degenerating motor control and loss of sensation (Atkinson, Hamborsky, and Wolfe, eds. *Diphtheria.* In: *Epidemiology and Prevention of Vaccine-Preventable Diseases.* 10$^{th}$ ed. 2007, Washington D.C.: Public Health Foundation. pp. 59-70). Diptheria is treated with an anti-toxin that neutralizes toxin that is not bound to tissues, as well as antibiotics to prevent further transmission (Mayo Foundation for Medical Education and Research, 2009. *Diphtheria*: Treatment and Drugs.)

2. *Clostridium* toxins. *C. difficile, C. botulinum, C. tetani,* and *C. perfringens* all produce protein toxins that cause symptoms ranging from abdominal cramps, diarrhea and vomiting associated with food poisoning, gas gangrene at the site of trauma or recent surgical wounds, spasms and rigidity of voluntary muscles, and colitis. These symptoms are all caused by clostridial extracellular protein toxins rather than by an immunological response to the bacterial infection itself or damage associated with bacterial growth in tissues (Madigan et al. *Brock: Biology of Microorganisms.* 12$^{th}$ ed. 2009, Pearson/Benjamin Cummings pp. 829-832).

3. *Pseudomonas aeruginosa* toxins. *Pseudomonas aeruginosa* is an opportunistic pathogen that secretes numerous extracellular proteins and enzymes that are virulence factors including: elastase, alkalin protease, a pore-forming cytotoxin, phospholipase C, and lechithinase (Pessi et al. (2001) *J. Bac.* 183:6676-6683). Once *P. aeruginosa* has colonized host tissue, these extracellular proteins and enzymes break down the host's physical barriers, damage host cells, and interfere with the host's immune response, collectively allowing disease to progress. *P. aeurginosa* also produces extracellular protein toxins (exotoxins) that mediate local and systemic disease processes.

4. Shiga toxins. *Shigella dysenteriae,* and the shigotoxigenis group of *Escherichia coli* (STEC), including serotype 0157:H7 and other enterohemorrhagic *E. coli,* produce large extracellular protein toxins that cause hemorrhagic colitis, kidney failure and death (Kaper and O'Brien, eds. *Escherichia coli* O 157:H7 and other Shiga Toxin-Producing *E. coli* Strains (1998), ASM Press (Herndon, Va.); and Frasher et al. (2006) *J. Biol. Chem.* 279:27511-27517). Shiga toxins inhibit protein synthesis by interfering with host ribosomes.

These are but a few examples of extracellular proteins and enzymes secreted by bacteria into tissues. Another extracellular enzyme is an iron reductase that is responsible for reducing Fe(III)→Fe(II), which is then bound and transported into the cell (Cowart (2002) *Archives of Biochemistry and Biophysics,* 400:273-281). Because iron is a required for bacterial growth, an extracellular enzyme that supplies iron to the infectious bacterium is important for bacterial growth.

Despite these examples, the majority of extracellular proteins and enzymes have functions that have not yet been characterized. Furthermore, little is known about the collective function of bacterial extracellular components or, more specifically, their function in terms of pathogenesis.

Vaccines

One mechanism used to halt the onset of pathogenesis and prevent disease is to improve host immunity by administering a biological preparation called a "vaccine" that establishes or improves immunity to a particular pathogen through the induction, or elicitation of an immunological response. Vaccines can be prophylactic (e.g., to prevent or ameliorate the effects of a future infection by any natural or "wild" pathogen) or therapeutic (e.g., vaccines against cancer, which are under investigation). Vaccines may comprise dead or inactivated microorganisms or purified products derived therefrom.

There are several types of vaccines currently in use, and follow different strategies to reduce risk of illness, while retaining the ability to induce a beneficial immune response. For instance, some vaccines contain killed microorganisms. These are previously virulent microorganisms which have been killed using chemicals or heat. Examples include vaccines against flu, cholera, bubonic plague and hepatitis A. Other vaccines contain live, attenuated microorganisms that have been cultivated under conditions that disable their virulence determinants. Alternatively, vaccines can comprise microorganisms that are closely-related, but less pathogenic than the organisms that cause the disease to produce a broad immune response. They typically induce infections and immunological responses without causing appreciable disease and are the preferred type of vaccines for use in healthy adults. Examples include vaccines for yellow fever, measles, rubella and mumps. The live attenuated tuberculosis vaccine called BCG, originally derived from cows, is immunogenic but does not cause extensive immunopathology.

Toxoids are inactivated toxic compounds, which are used in cases where the toxic compound, rather than the microorganism itself, cause illness. For example, the diphtheria vaccine is comprised of either formalin-treated diphtheria toxin or a recombinant toxin; neither is infectious, both stimulate the host's immune system to produce antibodies (Lobeck et al. (1998) *Infection and Immunity*. 66:418-423).

Vaccines need not contain a whole microorganism. Rather, a protein fragment of such microorganism can be used to illicit an immune response. Examples of such protein fragments used for vaccination are the surface proteins, suitably protein subunits, of Hepatitis B virus produced in yeast. Surface proteins with various functions are associated with the outer layer of both Gram-negative and Gram-positive bacteria. Many bacteria have mechanisms that impair antibody production by inducing suppressor cells, blocking antigen processing, and inhibiting lymphocyte mitogenesis. Some bacteria, such as, *Neisseria gonorrhoeae, Haemophilus influenzae, Proteus mirabilis*, clostridial species, and *Streptococcus pneumoniae* produce IgA-specific proteases that cleave and inactivate secretory IgA on mucosal surfaces. Other bacteria, such as pneumococci, meningococci, have capsules that prevent opsonic antibodies from binding. Typically protein or protein subunit vaccines are prepared using either surface proteins, external polysaccharides, or intracellular proteins.

For example, *Staphylococcus aureus* vaccines are presently available in the form of inactivated highly encapsulated *S. aureus* cells. Their efficiency for long-term treatment of disease, such as mastitis, has not been confirmed, and there is considerable variability in the structure of capsular polysaccharides which could limit the usefulness of this approach.

With respect to other bacteria of pathogenic importance for mammals vaccines comprising immunogenic virulence proteins are important. Such protein-based vaccines should be of particular value in the case of vulnerable subjects such as very young children, which are able to produce antibodies against foreign proteins. While bacterial proteins have been used to create vaccines, those proteins were intracellular or membrane bound, not secreted proteins. Accordingly, it is desirable to prepare bacterial vaccines constructed with at least one or more extracellular proteins to confer immunity against microorganism-associated infectious disease.

BRIEF SUMMARY OF THE INVENTION

The present invention provides a novel immunogenic composition for providing protection against microorganism-associated infectious disease and the methods associated with preparing and using such a composition. Specifically, the invention provides a new and surprising immunogenic composition comprising at least one extracellular microbial protein, wherein the extracellular protein(s) is involved in essential functions that are necessary for the growth of pathogenic microorganisms in a host, and these extracellular proteins are capable of producing an immune response that provide protection against infectious disease caused by these pathogenic microorganisms.

One aspect of the invention includes a method of making a novel immunogenic composition comprising at least one or more extracellular proteins produced by a microorganism for eliciting an immune response or a protective immunity against either Gram-negative or Gram-positive microorganisms. In one embodiment, the composition comprises at least fifty, at least twenty, or at least ten extracellular proteins. In an alternate embodiment, the composition comprises at least one to ten, three to eight or two to five extracellular proteins.

A related aspect encompasses an immunogenic composition comprising at least one extracellular protein isolated from a microorganism, the composition capable of eliciting an immune response or providing protective immunity in a subject against infectious diseases caused by Gram-negative or Gram-positive microorganisms. A further related aspect encompasses preparation of a vaccine using at least one extracellular protein in an amount effective for inhibiting growth of a microorganism within host tissues, thus preventing infection and the establishment of microorganism-associated disease.

Another aspect of the invention includes methods for administering an immunogenic composition capable of eliciting an immune response or providing protective immunity in a subject against microorganism-associated infectious diseases, wherein the composition comprises a therapeutically effective amount of at least one extracellular protein isolated from an infectious microorganism and an acceptable pharmaceutical carrier to a subject in need thereof.

In a related aspect, the invention provides immunogenic compositions capable of eliciting an immune response or providing protective immunity in a subject against Gram-negative and Gram-positive bacteria. In one embodiment, the immunogenic composition comprises extracellular proteins isolated from the supernatant fluids cultured from the bacteria. In one embodiment, the supernatant fluids include at least one extracellular protein ranging in molecular weight from about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa. Also encompassed here are methods for making the immunogenic composition of the present invention.

Another aspect of the invention provides a vaccine capable of eliciting an immune response or providing protective immunity in a subject against microorganism-associated infectious disease. The vaccine may, in one embodiment, comprise at least one extracellular microbial protein isolated from the supernatant fluid cultured from Gram-negative or Gram-positive microorganisms. When administered to a subject in need thereof, the vaccine is effective in the prevention of microorganism-associated infectious disease.

Another aspect of the invention provides a medicament useful for the inhibition, treatment, and/or prevention of an infectious microorganism. The medicament comprises an effective amount of the immunogenic composition or specific polypeptides of the present invention.

In another aspect, the invention provides a method for eliciting an immune response against either a Gram-negative or a Gram-positive bacterium in a mammal or other animal, the method comprising the step of administrating to the animal an effective amount of a composition of extracellular proteins preventing and/or treating a pathogen-associated disease in a mammal or other animal, as defined herein.

In a related aspect, the invention provides a method for preventing and/or treating a pathogen-associated disease in a mammal or other animal, comprising the step of administering to said animal an effective amount of an immunogenic composition comprising at least one extracellular protein capable of preventing and/or treating a pathogen-associated disease in a mammal or other animal, as defined herein.

In a related aspect, the invention provides a method for immunizing a mammalian or other animal host susceptible to disease caused by an infection by a Gram-negative or a Gram-positive pathogen. The method including (a) purifying bacterial extracellular proteins from at least one microorganism; (b) formulating the purified bacterial extracellular proteins in a predetermined effective amount, sufficient to be immunologically protective; and (c) administering to the mammalian or other animal host the formulated vaccine. In one embodiment, the vaccine is administered intracerebrally, intraperitoneally, intramuscularly or intradermally. In one embodiment, the host includes, yet is not limited to, humans, mice, cows, pigs, horses, chickens, cats or dogs. In one embodiment, the vaccine includes a pharmaceutically acceptable carrier.

Kits for detection, diagnosis and prevention of microorganism induced infectious disease are also encompassed here.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

The invention will be further understood in view of the following examples and the annexed figures.

DETAILED DESCRIPTION OF THE INVENTION

Figure 1A:
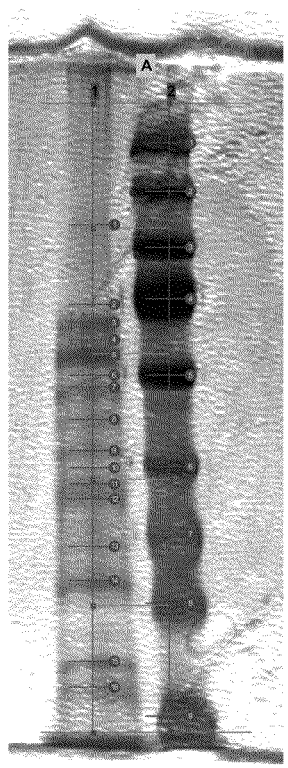
FIG. 1A is an image of an SDS-PAGE gel, showing the extracellular proteins in the immunogenic composition. The molecular weight standards are seen in lane No. 2 and the proteins that comprise the immunogenic compositions are shown in adjacent lane No. 1. The estimates of the molecular weights for the proteins presented in the immunogenic composition are provided in FIG. 1B.

The present invention encompasses immunogenic compositions and methods for making and using same to protect against microorganism-associated infectious disease. Specifically, the invention sets forth the new concept that extracellular microbial proteins, which are necessary for growth of pathogenic microorganisms in a host, are capable of producing an immune response to protect against infectious disease.

The invention therefore provides a novel immunogenic composition of one or more extracellular proteins which, upon introduction into a host, will confer immunity to that host, in the event the host is subsequently challenged by the same microorganism, which produced the protein(s). Although this finding is not established in the literature, it strongly suggests that the extracellular proteins are necessary for facilitating the pathogenic process, which involves the interaction of the microorganism with necessary tissues and other required molecular components of the cell or organism. This also facilitates and augments the growth of the microorganism in an intracellular or extracellular environment.

Although the role of extracellular microbial proteins as effectors of infectious processes is not recognized and represents a new area of study, the present invention now demonstrates that a multiple component mixture of extracellular protein(s) from Gram-negative and Gram-positive bacteria can serve as effective vaccines against subsequent challenge from bacteria in an experimental mouse model, where these bacteria are either of the same genus and species, or of entirely unrelated genera. Indicated proteins range in molecular weight from about 10,000 Da to about 24,000 Da, according to SDS-PAGE analysis upon silver stain. Also, Proteins ranging in size up to 220,000 Da have been identified using Western blot analysis. Data provided herein indicates that proteins ranging in size between 80 kDa to 140 kDa are involved in immunogenicity, and is explained in detail later. Such Proteins were identified via Western blot which is about 1,000 times more sensitive than a silver stain. In other embodiments, the extracellular protein ranges in size about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa.

The functions of these proteins are largely unknown. However, the vaccine trials described here for the first time suggest these proteins are essential for growth and pathogenesis of the infectious microorganisms. Antibodies produced in response to the at least one extra cellular protein in the vaccine neutralize the effects of such infectious protein(s); i.e., they preclude growth, infection and disease. The mechanisms by which this occurs are unknown at this time.

Bacterial extracellular proteins and enzymes participate in (a) the interaction of invading microorganism with host tissues; (b) the mobilization of essential nutrients from host tissues for the growth of the invading microorganisms; (c) the abrogation of the essential functions of the immune system; or (d) a combination thereof. Hence, the extracellular proteins and enzymes should function as an efficient vaccine. One rationale for this hypothesis is that if a host produces antibodies to extracellular proteins and/or enzymes that are essential for growth of the invading bacterium, and if those antibodies bind and neutralize the function of those extracellular proteins and/or enzymes, then the host should be protected from challenge by that bacterium.

Definitions

This invention is not limited to the particular methodology, protocols, and reagents described, as these may vary. The terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

As used herein and in the appended claims, the singular forms "a," "an," and "the" include plural reference unless the context clearly dictates otherwise. As well, the terms "a" (or "an"), "one or more," "at least one," "comprising," "including," "characterized by" and "having" can be used interchangeably herein.

Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Certain terms used herein are intended to have the following general definitions:

"Administering" or "administration" includes any means for introducing the immune composition or vaccine of the present invention into a subject. Examples include but are not limited to oral, buccal, sublingual, pulmonary, transdermal, transmucosal, as well as subcutaneous, intraperitoneal, intravenous, and intramuscular injection. compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

"Adjuvant" refers to a chemical or biological agent given in combination with one or more proteins, polynucleotides or polypeptides to enhance their immunogenicity.

"Antibody" refers to amino acid polymers that are produced by the immune system and can recognize and neutralize non-self (foreign) substrates, including, but not limited to, bacteria and viruses. Polyclonal, monoclonal and recombinant antibodies are encompassed here.

"Attenuation" is a modification that renders a microorganism or vector less pathogenic. An attenuated microorganism can establish an infection, but the risk of toxicity and other side-effects is decreased when the microorganism or vector is administered to the patient.

"Carrier" refers to a diluent, adjuvant, excipient or vehicle with which an attenuated virus or infectious DNA is administered. Such pharmaceutical carriers include sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

"Extracellular proteins" refers to proteins, polypeptides or truncated peptides that are synthesized within the bacterial cell and are subsequently transported to the exterior of the cell where they are released into the extracellular milieu. Alternatively, suitable extracellular proteins can be synthetically or recombinantly produced. Extracellular proteins are present in the immunogenic preparation used to confer immunity against infectious disease causing microorganisms.

As to extracellular proteins, five multiple component mixtures consisting of at least one extracellular protein have been determined to serve as effective vaccines against subsequent challenges by either the organism from which the extracellular proteins were derived, or from totally unrelated organisms in an experimental mouse model. The extracellular proteins of the present invention, and functional polypeptide fragments thereof, range in molecular weight from about 10,000 Da to about 220,000 Da, according to SDS-PAGE and Western blot analysis. In other embodiments, the extracellular protein ranges in size about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa. The functions of these proteins are largely unknown. However, on the basis of the vaccine trials it is implicit that these proteins are essential in facilitating the growth and pathogenesis of the infectious organism. The role of extracellular microbial proteins as effectors of infectious processes is essentially not recognized and represents a new area of study. It is concluded that these proteins are necessary for a number of bacteria to potentiate pathogenesis.

"Formulated" means preparing the composition for administration as a vaccine, using such methods commonly known to one of skill in the art.

"Gene" refers to a nucleic acid sequence that encodes for at least one polypeptide, or an RNA molecule.

"Host", "subject" or "patient" refers to a recipient of the present immunogenic compositions. Exemplary hosts are animals including, but not limited to, primate (human), rodent (mouse or rat), bovine (cow), horse, dog, cat, fish, goat, rabbit, pigeon, poultry (chicken), sheep, swine (pig) and elephant. In one embodiment of the present invention, the host is a preferably a mammal and most preferably a human.

"Immunogen" shall mean any substrate that elicits an immune response in a host. Immunogens of the present invention include, but are not limited to, major extracellular proteins and their recombinant forms or a particular molecular structure that constitutes an antigenic determinant, or epitope, that is derived from the proteins produced by bacterial pathogens.

"Immunogenic composition" comprises a recombinant vector with or without an adjuvant, such as an intracellular pathogen, that expresses and/or secretes an immunogen in vivo wherein the immunogen elicits an immune response in the host. The immunogenic compositions disclosed herein may be a prototrophic, auxotrophic or metabolically impaired transformant. The immunogenic compositions of the present invention may or may not be immunoprotective or therapeutic. When the immunogenic compositions of the present invention prevent, ameliorate, palliate or eliminate disease from the host, then the immunogenic composition may optionally be referred to as a vaccine. However, the term immunogenic composition is not limited to a vaccine; it can refer to a preparation of extracellular proteins capable of conferring immunity against disease caused by microorganisms.

"Inhibiting" refers to a process by which the infectious, pathogenic machinery of a microorganism is abrogated.

"Immune response" refers to a T cell response or increased serum levels of antibodies to an antigen, or to the presence of neutralizing antibodies to an antigen, such as an extracellular polypeptide or mixture of polypeptides or proteins from a microorganism.

"Isolating" or "Isolated" refers to a nucleic acid sequence that is identified and separated from at least one component or contaminant with which it is ordinarily associated in its natural source. Isolated nucleic acid as such is present in a form or setting that is different from that in which it is found in nature.

"Microorganism" and "pathogen" broadly refer to prokaryotic pathogenic microorganisms, either with or without plasmids or other extraneous genetic elements. Microorganisms encompassed within the scope of this invention include both Gram-negative and Gram-positive bacteria, non-limiting examples of which are listed below in Table 1. This table lists pathogenic bacteria known to produce extracellular proteins that have a reasonable expectation of vaccination success using the instant method of vaccine production.

It is hypothesized that microorganisms that produce extracellular proteins use these proteins for interactions with tissues, procurement of nutrients from the host and as facilitators of the infectious, pathogenic process. Thus, the abrogation of the function of these extracellular proteins by either one or more antibodies, or a small ligand inhibitor, or the inhibition of tissue interactions by a T-cell response will render the pathogenic microorganism unable to cause disease.

TABLE 1

Pathogenic Bacteria Known to Produce Extracellular Proteins.

Gram-negative
Rods & Cocci

*Aeromonas* spp. (heterotroph)
*Bordetella* spp.
*Brucella* spp.
*Haemophilus* spp.
*Neisseria* spp.
*Bacteriodes* spp.
*Borrelia* spp.
*Leptospira* spp.
*Pseudomonas* spp.
*Pseudomonas aeruginosa*
*Cardiobacterium* spp. (aerobic bacilli)
*Branhamella* spp. (aerobic cocci)
*Chromobacterium* spp. (facultative anaerobe *coccobacillus*)
*Flavobacterium* spp.
*Francisella* spp. (facultative intracellular aerobe)
*Streptobacillus* spp. (facultative anaerobe)
Enterics

*Citrobacter* spp.
*Enterobacter* spp.
*Escherichia* spp.
*Edwardsiella* spp.
*Klebsiella* spp.
*Proteus* spp.
*Salmonella* spp.
*Serratia* spp.
*Shigella* spp.
*Yersinia* spp.
*Acinetobacter* spp. (bacilli)
Helical and Curved Bacteria

*Campylobacter* spp.
*Treponema* spp.
*Borrelia* spp.
*Leptospira* spp.
*Vibrio* spp. (curved rod, facultative anaerobe)
Obligate intracellular parasites

*Coxiella* spp.
*Rickettsia* spp.
*Bartonella* spp. (facultative)
*Morazella* spp.
*Pasteurella* spp. (opportunistic path, rod/*coccobacillus*)
Gram-positive
Cocci

*Streptococcus* spp.
*Staphylococcus* spp.
*Peptococcus*
*Peptostreptococcus*
Actinomycetales and Relatives

*Actinomyces* spp.
*Corynebacterium* spp.
*Mycobacterium* spp.
*Norcardia* spp.
*Bifidobacterium* spp.
*Prioionibacterium* spp.
Endospore formers

*Bacillus* spp.
*Clostridium* spp.
Rods

*Erysipelothrix* spp.
*Lactobacillus* spp.

TABLE 1-continued

Pathogenic Bacteria Known to Produce Extracellular Proteins.

*Listeria* spp.
*Listeria monocytogenes*
No Gram Stain
Obligate intracellular parasites

*Chlamydia* spp.
*Ureaplasma* spp.
*Mycoplasma* spp.

"*Salmonella typhimurium*" is a Gram-negative, fermentative, facultatively aerobic rod shaped bacterium that is a member of the Family Enterobacteriaceae, is cylindrical in shape and measures about 2 microns by 0.5 microns, which is much smaller than the eukaryotic cells of higher organisms such as humans. *S. typhimurium* is typically thought of as an enteric bacterium, where 'enteric' is defined as a Gram-negative microbe that is facultatively aerobic, oxidase negative and typically found in the intestinal track of mammals.

*Salmonella typhimurium* 14028 (*Salmonella enterica* subsp. *enterica* serovar *Typhimurium* str. 14028S) genome (GenBank Accession no. CP001363) is 4,870,265 base pairs in size and was described in Jarvik et al. J. Bacteriol. 192 (2), 560-567 (2010). It is envisioned that based on the cited references and GenBank Accession numbers, a skilled person could identify the extracellular proteins that are leading to the immunogenic protection.

The *Salmonella typhimurium* LT2 (*Salmonella enterica* subsp. *enterica* serovar *Typhimurium* str. LT2) genome (GenBank Accession no. AE006468) is 4,857,432 base pairs in size and was described in McClelland et al. Nature, 413 (6858), 852-856 (2001).

In culture, *S. typhimurium* will grow on artificial media to form colonies. *S. typhimurium* multiplies in the gastrointestinal tract of many animal species without causing disease, but in humans its growth causes gastroenteritis. Six to forty-eight hours after ingestion of contaminated water or food (usually poultry or beef), illness may begin with nausea and vomiting, often followed by diarrhea. In healthy adults the disease is usually self-limiting with good medical care, but it is more serious in the young, the old and those with underlying medical conditions. The case-fatality ratio can be as high as 5%-10% in nurseries and nursing homes.

Isolations of *Salmonella* causing gastroenteritis in humans have increased in recent years in developed countries, primarily because methods of animal husbandry, food preparation and distribution encourage the spread of *Salmonella*. *Salmonella typhi* is the causative agent of typhoid fever in humans. Typhoid fever is caused by an intracellular infection of the Peyer's patches of the small intestine, although infection can spread to other sites such as the spleen, liver, lungs and urinary tract.

Resistance to *Salmonella* infection can be both humoral and cellular, dependent on the mode of infection. For example, the extracellular infection relies on antibodies for protection, while the intracellular infection relies on principally a cell-mediated response (Mackaness et al. (1966) *J. Exp. Med.*, 124: 573-583).

"*Vibrio parahaemolyticus*" is a fermentative, Gram-negative, facultatively aerobic curved rod that is a member of the Family Vibrionaceae. It is not typically classified as an enteric microbe as it is oxidase positive and is found in marine environments, or in brackish waters. The organism can colonize shell fish and sea food and cause infections in individuals who ingest these food products as raw or undercooked. Gastrointestinal symptoms can range from mild, to significant, to fatal. If an infection goes systemic this can lead to an extreme outcome where limbs have to be amputated, and a fatal infection occurs. *Vibrio parahaemolyticus* strain RIMD 2210633 genome includes chromosome 1 (GenBank accession no. BA000031), which is 3,288,558 base pairs in size and chromosome 2 (GenBank accession no. BA000032), which is 1,877,212 base pairs in size. Chromosomes 1 and 2 were described in Nasu et al. J. Clin. Microbiol. 38 (6), 2156-2161 (2000).

"*Vibrio cholera*" is another member of the vibrios family of microorganisms. There have been seven confirmed cholera pandemics since the early 1800's, and the World Health Organization estimates that there are 3-5 million cholera cases per year world wide with 100,000-120,000 deaths.

"*Pseudomonas aeurginosa*" is an ubiquitous nonfermentative, Gram-negative, oxidase positive rod shaped bacterium that is found in soils, fresh waters, the atmosphere, and on skin. It is an aerobic organism although some strains can grow anaerobically under the appropriate conditions. It is a member of the Family Pseudomonadaceae. Thus, it is not thought of as an enteric microbe as it is found throughout the environment. It is not an obligate pathogen but can cause serious, often fatal infections. This is because it is inherently antibiotic resistant, and secretes numerous extracellular proteins and enzymes that consist of toxins and enzymes that can degrade red blood cells and other tissues. The organism typically can cause urinary track, lung, bone, blood, and other soft tissue infections resulting in fatal outcomes. Patients with cystic fibrosis often acquire *P. aeurginosa* infections in their lungs, which are very difficult to treat because of the antibiotic resistant nature of the organism and the location of the organism within the thick mucus in the lungs that accompanies this disease. Often individuals who have cystic fibrosis succumb to *P. aeurginosa* infections. The *Pseudomonas aeruginosa* strain PAO1 genome (GenBank Accession no. AE004091) is 6,264,404 base pairs in size and was described in Stover et al. Nature, 406 (6799), 959-964 (2000).

"*Staphylococcus aureus*" is a facultatively aerobic, pathogenic Gram-positive cocci that is a member of the Family Staphylococcaceae. The organism can be found on the skin and within the nasal cavity. It can cause skin infections such as pimples, boils, carbuncles, scalded skin syndrome, and abscesses, in addition to causing a toxic food born illness. If a *S. aureus* infection goes systemic it can cause extremely serious bone and joint, lung, blood, and other organ and tissue infections. It was in the early 1960's that a strain of *S. aureus* was identified that was resistant to penicillin, and was given the name MRSA, which stands for methicillin-resistant *Staph aureus*. It has been within the past 10-20 years that strains of MRSA have emerged that are increasingly resistant to the penicillins, which has propelled MRSA to a major, worldwide public health hazard. Individuals infected with MRSA are considered to have serious infections, not only because they might transfer this organism to others, but also because the infection is very difficult to treat. The *Staphylococcus aureus* FPR3757 (*Staphylococcus aureus* subsp. *aureus* USA300_FPR3757) genome (GenBank Accession no. NC_007793) is 2,872,769 base pairs in size and was described in Diep et al. Lancet 367 (9512), 731-739 (2006).

"*Listeria monocytogenes*" is a small, cocci shaped Gram-positive rod shaped bacterium that is a member of the Family Listeriaceae. This organism has been known to cause spontaneous abortions in humans and animals, and within the past 25-30 years has been identified as an organism that can cause serious food born illness. It can also cause meningitis in newborns, or the elderly, with fatal outcomes. *L. monocyto-*

*genes* is described as an intracellular pathogen, meaning the organism either invades host cells, or is phagocytosed by professional phagocytes and often resists killing once in an intracellular state. The organism can move from cell to cell without becoming extracellular. Immunity is through by a cell-mediated response involving T-cells and activated macrophages and does not involve antibodies. The *Listeria monocytogenes* EGD-e genome (GenBank accession no. AL591824) is 2,944,528 base pairs in size and was described in Glaser et al. Science 294 (5543), 849-852 (2001). The *Listeria monocytogenes* 10403S genome (GenBank accession no. AARZ00000000) is 2,873,541 base pairs in size and was submitted by Borowsky al. from the Broad Institute Genome Sequencing Platform on Aug. 18, 2006.

"Pharmaceutically acceptable" means approved by a regulatory agency of the federal or a state government or listed in the U.S. Pharmacopeia or other generally-recognized pharmacopeia for use in animals and, more particularly, in humans.

"Pharmaceutically acceptable carrier" means, but is not limited to, a vehicle for containing a DNA plasmid that can be injected into a mammalian host without adverse effects. Suitable pharmaceutically acceptable carriers known in the art include, but are not limited to, gold particles, sterile water, saline, glucose, dextrose or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like. In general, a diluent or carrier is selected on the basis of the mode and route of administration, and standard pharmaceutical practice.

"Preventing" refers to a process by which a microorganism-associated disease is obstructed or delayed. The compositions and vaccines of the invention comprise extracellular proteins isolated from a microorganism.

"Protection" or "protective immunity" refers to the ability of the serum antibodies, or T cell response, or both, induced during immunization to protect (partially or totally) against disease or death caused by an infectious agent. That is, a mammal immunized by the vaccines of the invention will experience limited growth and spread of an infectious microorganism.

"Sample" is used in its broadest sense and is meant to include a specimen or culture obtained from any source, including biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective dose" or "therapeutically effective amount" means a dose or amount that, when administered to a subject for treating a disease, produces the desired effect for which it is administered (such as, for instance, effect such treatment for the disease). The "therapeutically effective amount" will vary depending on the compound, the disease state being treated, the severity or the disease treated, the age and relative health of the subject, the route and form of administration, the judgment of the attending medical or veterinary practitioner, and other factors, and will be ascertainable by one skilled in the art using known techniques (see, for example, Lloyd (1999) "The Art, Science and Technology of Pharmaceutical Compounding").

"Treating" or "treatment" refers to a process by which the symptoms of a microorganism-associated disease are ameliorated or completely eliminated. It describes the management and care of a subject for the purpose of combating a given disease, condition, or disorder. The terms embrace both preventative, i.e., prophylactic, and palliative treatment. Treating includes the administration of a compound of the present invention in an attempt to alter the natural course of the individual or cell being treated and may be performed either for prophylaxis or during the course of clinical pathology. Desirable effects include preventing occurrence or recurrence of disease, alleviation of symptoms, and diminishment of any direct or indirect pathological consequences of the disease, preventing metastasis, lowering the rate of disease progression, amelioration or palliation of the disease state, remission or improved prognosis.

"Vaccine" is a composition for human or animal use, which is administered to effectuate specific immunological reactivity against a particular target or group of targets. The immunological reactivity may be antibodies or cells (e.g., B cells, plasma cells, T helper cells, cytotoxic T lymphocytes and their precursors) that are immunologically reactive against the target. The immunological reactivity may be desired for experimental purposes, treatment of a particular condition, the elimination of a particular substance, or prophylaxis. An active vaccine is a vaccine intended to elicit an immune response in the recipient that persists in the absence of the vaccine components.

Vaccine preparation is generally described in "New Trends and Developments in Vaccines", edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Vaccines can be proteins derived from the cell membrane, cell wall or cytoplasmic proteins, whether free or in association with subcellular structural components. As described here, vaccines can also be obtained from extracellular secreted bacterial proteins. They can also comprise polysaccharide, DNA or RNA. Vaccines can be live attenuated bacteria or active attenuated viruses, which when administered will induce an infection but not generally cause disease.

The vaccine of the invention, and vaccines made using the method of the invention, can be administered in amounts and by using methods that can readily be determined by persons of ordinary skill in this art. The amount of protein in each vaccine dose is selected as an amount which induces an immunoprotective response without significant adverse side effects in typical vaccines. Such amount will vary depending upon which specific immunogen is employed and how it is presented. Generally, it is expected that each dose will comprise from about 5 µg to about 100 µg of total protein. Preferably 20 µg of total protein, most preferably 50-100 µg of total protein can be used. An optimal amount for a particular vaccine can be ascertained by standard studies involving observation of appropriate immune responses in subjects.

The vaccines can be administered and formulated, for example, as a supernatant fluid harvested from cell cultures.

The vaccine can be administered by, for example, subcutaneous, intramuscular, intraperitoneal or intradermal routes. In addition, a mucosal route, such as the oral or nasal route, can be selected. Selection of an appropriate amount (concentration or total volume) of vaccine to administer can be determined by those skilled in this art, and this amount can vary due to numerous factors, e.g., the size and general health of the subject to whom the vaccine is to be administered. Following an initial vaccination, subjects may receive one or several booster immunizations, adequately spaced in time.

Adjuvants are typically used to boost immune response. Most often aluminum adjuvants are used, but adjuvants like squalene are also used in some vaccines and more vaccines with squalene and phosphate adjuvants are being tested. Also, several preservatives are available for use in vaccines, including thiomerosol, phenoxyethanol and formaldehyde.

Delivery mechanisms for vaccines include but are not limited to auto-disable (AD) syringes and safety boxes, monodose prefilled injection devices, needle-free injections, point-of-use sharps processing, thermostable vaccines, and vaccine vial monitors. Nasal spray vaccines are also envisioned.

There are several new delivery systems in development which will hopefully ease vaccine delivery. Possible methods include liposomes and ISCOM (immune stimulating complex), oral vaccines, which circumvent the risk of blood contamination, or a microneedle approach, which is still in stages of development.

Embodiments of the Invention

In one embodiment, the present invention provides a novel method of making an immunogenic composition capable of protecting a subject from infectious disease. The method comprises culturing a microorganism under conditions sufficient to yield a supernatant fluid and isolating the supernatant fluid from the culture, wherein the supernatant fluid comprises at least one extracellular protein capable of protecting a subject from infectious disease. In one embodiment, the supernatant fluid comprises at least 50 extracellular proteins, while in alternate embodiments, the supernatant fluid comprises at least two to ten extracellular proteins. The extracellular proteins can range in molecular weight from about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa. Any microorganism can be used in the method of the present invention, although in one embodiment, the microorganism is a Gram-negative or a Gram-positive bacteria, including, but not limited to *Pseudomonas aeurginosa, Vibrio parahaemolyticus, Salmonella typhimurium, Staphylococcus aureus*, or *Listeria monocytogenes*. The extracellular proteins are necessary for facilitating the pathogenic process, which involves the interaction of the microorganism with necessary tissues and molecular components of the cell or organism. This also facilitates and augments the growth of the microorganism in an intracellular or extracellular environment.

The humoral and/or the cell-mediated immune response to these extracellular immunogenic components abrogate the function of these infectious proteins, thus interfering with the establishment of the disease state in the host. This abrogation of function is likely because the infectious proteins of the microorganism are unable to interact with essential host tissues or host molecular components. The growth of the microorganism can also be diminished or inhibited resulting in the protection of the host from the infectious disease.

Extracellular proteins are used by all microorganisms for interactions with tissues, procurement of nutrients from the host, protection from the immune system and as facilitators of the infectious, pathogenic process. Thus, the abrogation of the function of these extracellular proteins by either one or more antibodies, a cell-mediated immune response or a small ligand inhibitor will render the pathogenic microorganism unable to cause disease.

In a related embodiment, the invention provides a novel immunogenic composition capable of protecting a subject from microorganism-associated infectious disease. The immunogenic composition comprises at least one extracellular protein isolated from a microorganism, wherein when the at least one extracellular protein is introduced into a subject, it is capable of protecting the subject from microorganism-associated infectious disease. The immunogenic composition may protect a subject from microorganism-associated infectious disease caused by the same microorganism from which the extracellular protein of the composition was produced. However, the immunogenic composition of the present invention may also protect a subject from microorganism-associated infectious disease caused by a different microorganism from which the extracellular protein of the composition was produced. The extracellular protein of the immunogenic composition may be isolated from any microorganism, although in one embodiment, the microorganism is a rod or cocci-shaped Gram-negative bacteria, including, but not limited to *Pseudomonas aeurginosa, Vibrio parahaemolyticus, Salmonella typhimurium, Staphylococcus aureus*, or *Listeria monocytogenes*. In one embodiment, the at least one extracellular protein is isolated from supernatant fluid cultured from the microorganism, wherein the supernatant fluid comprises at least one extracellular protein ranging in molecular weight from about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa. In one embodiment, the subject is selected from the group consisting of humans, mice, cows, pigs, horses, chickens, cats and dogs.

In one embodiment, the present invention also provides a novel vaccine capable of protecting a subject from microorganism-associated infectious disease. The vaccine comprises at least one polypeptide, a functional fragment thereof or epitope/antigenic determinant isolated from an extracellular protein preparation isolated from a microorganism, wherein at least one polypeptide ranges in molecular weight from about 10 kDa to about 200 kDa, and a pharmaceutically-acceptable carrier. In alternate versions the extracellular protein ranges in size from about 20 kDa to about 180 kDa, from about 40 kDa to about 160 kDa, from about 60 kDa to about 140 kDa, or from about 80 kDa to about 120 kDa. The extracellular protein of the immunogenic composition may be isolated from any microorganism, although in one embodiment, the microorganism is a Gram-negative or a Gram-positive bacteria, including, but not limited to *Pseudomonas aeurginosa, Vibrio parahaemolyticus, Salmonella typhimurium, Staphylococcus aureus*, or *Listeria monocytogenes*. A recombinant protein is also encompassed by the present invention.

In one embodiment, the present invention also provides a novel method of eliciting an immune response against a microorganism in a mammal. The method comprises administrating to the mammal an effective amount of an immunogenic composition comprising at least one extracellular protein isolated from supernatant fluid cultured from a microorganism; and determining the immune response to the composition. The extracellular protein of the immunogenic composition may be isolated from any microorganism, although in one embodiment the microorganism is a Gram-negative or a Gram-positive bacteria, including, but not limited to *Pseudomonas aeurginosa, Vibrio parahaemolyticus, Salmonella typhimurium, Staphylococcus aureus*, or *Listeria monocytogenes*. In one embodiment, the supernatant fluid includes one or more extracellular proteins ranging in molecular weight ranging from about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa. In one embodiment, the administering step is performed intracerebrally, intramuscularly, intraperitoneally or intradermally.

In one embodiment, the present invention provides a novel method for preventing and/or treating a pathogen-associated disease in a subject, the method comprising the step of administering to the subject an effective amount of an immunogenic composition capable of protecting a subject from microorganism-associated infectious disease. The immunogenic composition comprises at least one extracellular protein isolated from a microorganism, wherein when the at least one extracellular protein is introduced into a subject, it is capable of protecting the subject from microorganism-associated infectious disease. The immunogenic composition may protect a subject from microorganism-associated infectious disease caused by the same microorganism from which the extracellular protein of the composition was produced. However, the immunogenic composition of the present invention may also protect a subject from microorganism-associated infectious disease caused by a different microorganism from which the extracellular protein of the composition was produced. The extracellular protein of the immunogenic composition may be isolated from any microorganism, although in one embodiment, the microorganism is a rod or cocci-shaped Gram-negative bacteria. The administering step may be performed intracerebrally, intramuscularly, intraperitoneally or intradermally.

In one embodiment, the present invention provides a novel method for immunizing a subject susceptible to disease caused by a pathogen from either a Gram-negative or a Gram-positive bacteria. The method comprises isolating at least one bacterial extracellular protein reactive to the pathogen from either a Gram-negative or a Gram-positive bacteria; formulating the at least one isolated bacterial extracellular protein in a predetermined effective amount, such that the extracellular protein is immunologically protective; and administering the formulated extracellular protein to the subject, such that the subject is immunized to disease caused by the pathogen from either a Gram-negative or a Gram-positive bacteria, including, but not limited to *Pseudomonas aeurginosa, Vibrio parahaemolyticus, Salmonella typhimurium, Staphylococcus aureus*, or *Listeria monocytogenes*. In one embodiment, the pathogen is a member of the genus *Salmonella*, and the at least one extracellular protein is isolated from supernatant fluid cultured from a Gram-negative or a Gram-positive bacteria, wherein the supernatant fluid includes one or more extracellular proteins ranging in molecular weight from about 10 kDa to about 200 kDa. In alternate versions the extracellular protein ranges in size from about 20 kDa to about 180 kDa, from about 40 kDa to about 160 kDa, from about 60 kDa to about 140 kDa, or from about 80 kDa to about 120 kDa. The subject may be selected from the group consisting of humans, mice, cows, pigs, horses, chickens, cats and dogs.

In one embodiment, the invention provides a DNA construct having a nucleic acid sequence encoding an immunogenic peptide from the extracellular protein preparation wherein the DNA construct, upon administration and uptake by cells of a host, expresses the immunogenic peptide which induces a protective immune response to bacterial infection, preferably caused by Gram-negative or Gram-positive bacteria. In a related embodiment, in addition to an extracellular peptide, the DNA construct further optionally includes a eukaryotic promoter and/or a secretion sequence.

Another embodiment of the invention includes kits for detecting bacterial infections and/or immunizing against infectious microorganisms encompassed below. Specifically, the present invention provides a kit comprising, in at least one container, a composition for detecting, diagnosing and/or inhibiting microorganism induced infectious disease in animals comprising an effective amount of at least one inactivated isolated bacterial extracellular protein, polypeptide, or polynucleotides of the present invention and/or a pharmaceutically acceptable carrier. The kit may also include a set of printed instructions indicating that the kit is useful for detecting, diagnosing and/or preventing infectious disease in animals. The kit may further comprise a means for dispensing said composition. Bacterial polypeptides, or nucleotide sequences can be determined using antibodies, PCR, hybridization techniques, and other detection methods known to those of skill in the art.

A related embodiment provides a diagnostic method and corresponding test kit for use to detect antibodies against the serologically relevant immunodominant epitope or extracellular protein marker(s), therewith providing methods and means to execute a method for control and/or eradication of specific types of bacterial infections. The kit would include components, such as, antibodies, PCR primers, probes for hybridization, and other detection tools known to those of skill in the art. Such a kit would be useful to the medical industry because it is envisioned that in some cases extracellular proteins from infectious microorganisms are specific to the organism producing them.

One embodiment of the present invention is based, in part, on the following experimental results, which describe a method of preparing and administering an effective amount of the novel immunogenic composition and vaccine of the present invention to a subject, resulting in the vaccinated mammals having immunity against microorganism-associated infectious disease.

EXAMPLES

The following represents a protocol developed to obtain extracellular proteins and enzymes from, for instance, the Gram-negative organisms including *S. typhimurium* strains 14028s (virulent) and LT2 (avirulent), *Pseudomonas aeurginosa* strain PAO1, and *Vibrio parahaemolyticus* strain RIMD 2210633.

Vaccine Preparation

A virulent strain of *S. typhimurium*, 14028s, was grown in M9 defined medium at 37° C. at 200 rpm. Initially, the supernatant fluid was harvested at an absorbance (660 nm)=0.8. (See Sambrook (2001) *Molecular Cloning, A Laboratory Manual*. 3$^{rd}$ ed. Cold Spring Harbor Laboratory Press. p A2.2). The culture was placed on ice, the cells were centrifuged at 4° C. and the supernatant fluid was collected. The supernatant fluid was further processed by filtration using a 0.45 μm Durapore membrane filter—PVDF (polyvinylidene fluoride; Millipore, Billerica, Mass.). PVDF filters are known in the art as extremely low protein binding filters that are chosen for use when maximum protein recovery is important. A nitrocellulose filter (Millipore) was also tried, but it was found to interfere with the isolation process because it absorbed proteins from the supernatant fluid.

Figure 2:
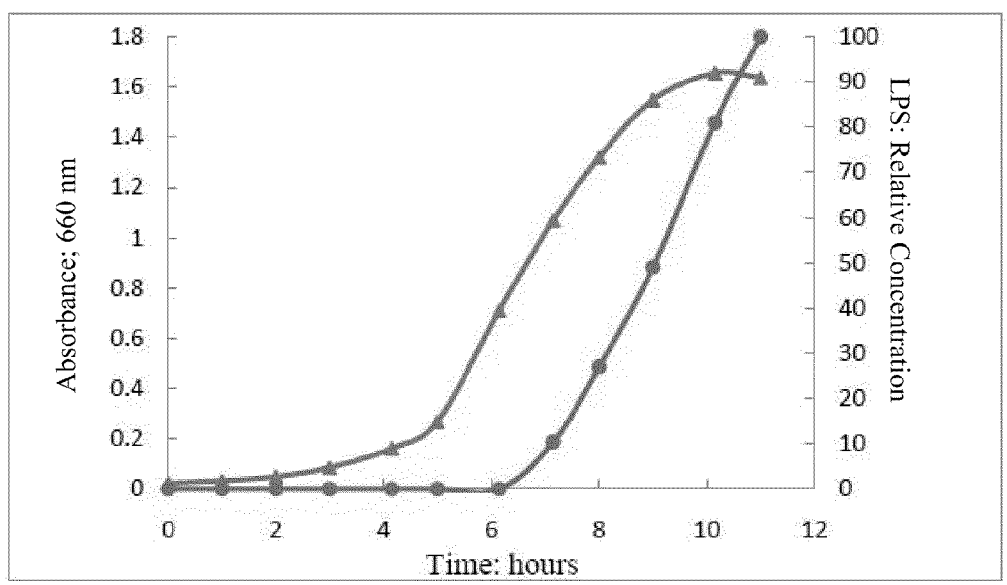
FIG. 2 illustrates LPS in supernatant fluids as a function of cell growth.

As the fluid was concentrated an extremely viscous material appeared that bound the proteins and rendered them unusable. After significant experimentation it was determined that this material was lipopolysaccharide (LPS). We carried out a study whereby we measured LPS in supernatant fluids as a function of cell growth, as shown in FIG. 2. In this experiment S. typhimurium, strain LT2, was grown in M9 medium at 37° C. and 200 rpm. At hourly intervals an absorbance reading at 660 nm was taken and a sample of the culture was collected and centrifuged at 14,000 rpm in a microfuge. The supernatant fluid was collected and filtered through a sterile 0.22 µm PVDF filter, and then stored at –20° C. until analysis for LPS, which was carried out by measuring the affect on ATP dependent chemoluminous intensity. The highest chemoluminous intensity occurs in the complete absence of LPS, and the intensity decreases as LPS increases.

In FIG. 2 growth is indicated by ▲-▲ and relative LPS concentration is indicated by ●-●. Here we see that LPS is not found in supernatant fluids of S. typhimurium, LT2 prior to about 6 hours of growth, which corresponds to an absorbance (66 nm)=0.71. This is also about mid-exponential phase of growth and suggests that LPS release is not simply a nonspecific release due to dying cells. Rather, this suggests that this release occurs in a manner suggestive of the release of a secondary metabolite, although the mechanism was not investigated as part of this study. Rather, this demonstrates that significant amounts of LPS are released from Gram-negative bacteria during growth, and that by harvesting the supernatant fluid prior to release, one can preclude the majority of contaminating LPS with the vaccine proteins. None the less, an affinity resin was prepared that specifically removed LPS and was used to treat the supernatant fluids of other Gram-negative bacteria used in vaccine production, and is described below. This is necessary to ensure that LPS has been removed from these preparations.

To remove soluble LPS from the sample, an affinity resin was prepared by covalently linking Polymyxin B, a cyclic amphipathic peptide antibiotic known in the art to bind LPS, to CNBr-activated Sepharose 4 Fast Flow agarose beads (GE Healthcare, Piscataway, N.J.). The filtered supernatant fluid was slowly passed over the affinity resin to remove soluble LPS, which is toxic to animals and must be removed prior to vaccine preparation. Supernatant fluid collected from the affinity column was again passed through a 0.45 µm PVDF filter. The supernatant fluid was then concentrated by using a stirred-cell concentrator using a 10,000 molecular weight cut-off filter (Millipore).

Affinity binding, filtration and stirred-cell concentration were carried out at 4° C. In a typical preparation, 3 L of supernatant fluid was treated as above and resuspended to 50 ml with sterile phosphate buffered saline (PBS; 50 nM phosphate, 0.85% NaCl), pH 7.4. The sample suspended in PBS, referred to herein below as the "vaccine preparation", was passed through a sterile 0.45 µm PVDF syringe filter in a sterile environment. The vaccine preparation was aliquoted in 7.0 ml volumes into Wheaton sterile rubber-lined screw-capped autoclavable borosilicate glass vials (Wheaton Science Products, Millville, N.J.) and stored at –20° C. Sterility tests of the vaccine preparation were carried out by plating 50 µl on tryptic soy agar (TSA) followed by incubation at 37° C. for 24 h. A Bradford protein assay was carried out to determine the total protein content of the sample, in addition to SDS-PAGE to determine the molecular weights of individual proteins in the sample.

Preparation of the Challenge Cells

S. typhimurium 14028s was grown in M9 medium at 37° C., 200 rpm, to an absorbance of 0.8 at 660 nm twice with sterile water by centrifugation, and resuspended in sterile PBS to the desired concentration using techniques known to those skilled in the art. These washed S. typhimurium 14028s cells were used to challenge the CD-1 mice.

Immunization of Mice

Outbred mice, strain CD-1 (Harland Teklad—Madison, Wis.) were used in this study. These mice were derived from Swiss outbred mice and this particular strain was begun in Philadelphia at the Institute for Cancer Research (ICR). CD-1 mice are known to those skilled in the art as a model for human infection (Chmiel et al. (1999) *A Resp. Cri. Care Med.* 160:2040-2047). Prior to immunizing CD-1 mice with the vaccine preparation, a $LD_{50}$ study was carried out to quantitatively determine the virulence of S. typhimurium 14028s. The $LD_{50}$ was determined to be $4 \times 10^3$ washed cells administered intraperitoneally (I.P.) in 35-50 g CD-1 mice.

In all vaccine trials, CD-1 mice, 35-50 g, were immunized multiple times with 200 µl of the vaccine preparation I.P. using a 22 g needle (Kendall Monoject, Mansfield, Mass.) attached to a 1.0 ml syringe (Becton Dickinson, Franklin Lakes, N.J.) (but see trial 3, first injection, for an exception). Upon completion of the prescribed immunization schedules, mice were challenged with S. typhimurium by injection with 200 µl of washed S. typhimurium 14028s cells I.P. at desired concentrations. Mice were then observed for Days 21-30, over which time healthy/sick and survivorship data were collected. In each trial an equal number of CD-1 mice, 35-50 g, were observed as controls. Vaccine trial data, consisting of immunization schedules and challenge phase, are provided herein below. Two independently-generated vaccine preparations were used in the trials. The protein concentration of the first vaccine preparation, used in trial 1, trial 2, and the first and second injections in trial 3, contained 15.2 µg/ml, resulting 3.04 µg of protein administered in each 200 µl injection. The protein concentration of the second vaccine preparation, used for the third injection in trial 3, contained 9.6 µg/ml, resulting in 1.92 µg of protein administered in each 200 µl injection.

Vaccine Trial No. 1

Five male CD-1 mice were used for each treatment in trial 1. Five mice were immunized with 200 µl of the vaccine preparation I.P. on Day 1, Day 13, Day 23, and Day 27.

All 10 mice were then challenged with $4 \times 10^3$ washed S. typhimurium 14028s cells, administered in 200 µl I.P injections on Day 33.

To summarize the results of Trial No. 1, the 5 vaccinated CD-1 mice challenged with $4 \times 10^3$ S. typhimurium 14028s ($LD_{50}$) did not exhibit symptoms of illness at any point during the trial. The 5 control CD-1 mice, which were also challenged with $4 \times 10^3$ S. typhimurium 14028s ($LD_{50}$), became very ill 3-4 days following bacterial challenge, but none died. Mice that were very ill exhibited matted coats, dull eyes, stiff movements and a group behavior of huddling together, in contrast to healthy mice that had no changes in their coats or eyes, continued to run around the cage, continued to hang from upper bars and did not huddle together.

TABLE 2

Trial 1: Immunization schedule, challenge schedule and observations.

| Day | Vaccination treatment (n = 5) | Control (n = 5) |
|---|---|---|
| 1 | 200 µl injection of vaccine preparation #1 | |
| 13 | 200 µl injection of vaccine preparation #1 | |
| 23 | 200 µl injection of vaccine preparation #1 | |
| 27 | 200 µl injection of vaccine preparation #1 | |
| 33 | Bacterial challenge: I.P. injection 4 × 10³ washed S. typhimurium 14028s | Bacterial challenge: I.P. injection 4 × 10³ washed S. typhimurium 14028s |
| 34 | Healthy (n = 5) | Healthy (n = 5) |
| 35 | Healthy (n = 5) | Healthy (n = 5) |
| 36 | Healthy (n = 5) | Healthy (n = 0) Sick (n = 5) Initial stages of illness |
| 38 | Healthy (n = 5) | Healthy (n = 0) Sick (n = 5) Ill |
| 41 | Healthy (n = 5) | Healthy (n = 0) Sick (n = 5) Very ill. |
| 44 | Healthy (n = 5) | Healthy (n = 0) Sick (n = 5) Ill |
| 48 | Healthy (n = 5) | Healthy (n = 0) Sick (n = 5) Ill, but recovering. |
| 62 | Healthy (n = 5) | Healthy (n = 5) |

In Trial No. 1, an $LD_{50}$, i.e., $4 \times 10^3$ organisms were administered to the control and the vaccinated group. The expectation that the control group would experience a 50% mortality. However, this did not occur. Two mechanisms may account for the unexpected survivorship of the control mice in this trial. First, independent batches of S. typhimurium 14028s were used in determining the $LD_{50}$ and in the bacterial challenge. Variation in bacterial growth and time of harvest could be responsible for the absence of mortality. Second, the $LD_{50}$ experiment was performed using CD-1 female mice, while the challenge experiments were carried out using male CD-1 mice. This difference could also explain the absence of mortality.

Vaccine Trial No. 2

Seven male mice were vaccinated with 200 µl of vaccine preparation number 1 I.P. using a 22 gauge needle on: Day 1, Day 10, Day 15 and Day 34.

The mice were challenged with $1 \times 10^4$ washed S. typhimurium 14028s in 200 µl sterile PBS. Seven male mice of the approximate same weight were used as controls.

TABLE 3

Trial 2: Immunization schedule, challenge schedule and observations.

| Day | Vaccine treatment (n = 7) | Control (n = 7) |
|---|---|---|
| 1 | 200 µl injection of vaccine preparation #1 | |
| 10 | 200 µl injection of vaccine preparation #1 | |
| 15 | 200 µl injection of vaccine preparation #1 | |
| 34 | 200 µl injection of vaccine preparation #1 | |
| 36 | Bacterial challenge: I.P. injection 1 × 10⁴ washed S. typhimurium 14028s | Bacterial challenge: I.P. injection 1 × 10⁴ washed S. typhimurium 14028s |
| 37 | Healthy (n = 7) | Healthy (n = 7) |
| 38 | Healthy (n = 0), Sick (n = 7) | Healthy (n = 7) |
| 39 | Healthy (n = 0), Sick (n = 7) Ill, but recovering. | Healthy (n = 0), Sick (n = 7) Initial stages of illness. |
| 40 | Healthy (n = 7) | Healthy (n = 0) Sick (n = 6) Dead (n = 1) ill |
| 42 | Healthy (n = 6) Sick (n = 1) One aggressive mouse was chewing the backs of other mice; it was isolated to a second cage. | Healthy (n = 0) Sick (n = 5) Dead (n = 2) Very ill |
| 45 | Healthy (n = 6) Dead (n = 1) The isolated mouse died within 36 h of the onset of symptoms, which is not characteristic of infection. | Healthy (n = 0) Sick (n = 5) Dead (n = 2) Very ill |
| 47 | Healthy (n = 6) Dead (n = 1) | Healthy (n = 0) Sick (n = 5) Dead (n = 2) Very ill |
| 50 | Healthy (n = 6) Dead (n = 1) | Healthy (n = 0) Sick (n = 4) Dead (n = 3) Two mice very ill, two ill but recovering. |
| 52 | Healthy (n = 6) Dead (n = 1) | Healthy (n = 0) Sick (n = 4) Dead (n = 3) Two mice very ill, two ill but recovering. |
| 54 | Healthy (n = 6) Dead (n = 1) | Healthy (n = 0) Sick (n = 4) Dead (n = 3) All four mice recovering. |
| 57 | Healthy (n = 6) Dead (n = 1) | Healthy (n = 2) Sick (n = 2) Dead (n = 3) Two mice completely recovered, two nearing recovery. |

To summarize the results of Trial No. 2, seven male mice were vaccinated as indicated above and challenged with $1 \times 10^4$ washed S. typhimurium 14028s. Seven untreated males were also challenged with the same bacterial dose. Vaccinated mice became ill approximately thirty-six hours after challenge but recovered within two days of becoming ill. This was likely due to an immune reaction and not a consequence of the infection. This can be explained by a hyperimmune response where extracellular bacterial proteins may have been rapidly produced due to the growth state of the microorganism. This would have been immediately followed by a substantial antigen-antibody reaction, which would have transient, negative consequences. The fact that the mice recovered within two days and the controls did not become sick at the same time suggests that this was likely the case. Control mice began to appear ill from infection on Day 3 and became increasingly sick through Day 14, at which time two mice started to improve. A total of three mice died in the second trial and, at the conclusion of the trial, two mice regained full health and two mice were nearing recovery.

Vaccine Trial No. 3.

Ten male mice were vaccinated 3 times with 200 µl of vaccine. The first two vaccinations were with preparation number one, and the third vaccination was with preparation two, as shown in Table 4 below. The mice were challenged five days after the final vaccination. On Day 2 after the first vaccination the mice were showing early signs of illness. This early illness was likely due to an overdose of the vaccine; 1.0 ml syringes were unavailable on this date, thus the mice were injected with 200 µl of the vaccine preparation using a 10 ml syringe. Injection using the 10 ml syringe likely resulted in dosages greater than 200 µl in each mouse. Mice recovered from this overdose by Day 4. Overdose related symptoms were likely due to additional LPS that was not completely removed by the endotox column. One ml syringes were obtained and the mice were vaccinated an additional two times with no signs of illness. As mentioned hereinabove, the protein concentration of the second vaccine preparation was 9.6 µg/ml, which gave a total protein concentration of 1.92

μg/200 μl on the final vaccination; approximately 60% the concentration of the first vaccine preparation.

Mice were challenged with 2×10$^4$ washed *S. typhimurium* 14028s resuspended in 200 μl sterile PBS. Ten unvaccinated male mice of the approximate same weight were used as controls.

TABLE 4

Trial 3: Immunization schedule, challenge schedule and observations.

| Day | Vaccine treatment (n = 10) | Control (n = 10) |
|---|---|---|
| 1 | 200 μl injection of vaccine preparation #1 | |
| 40 | 200 μl injection of vaccine preparation #1 | |
| 54 | 200 μl injection of vaccine preparation #2 | |
| 59 | Bacterial challenge: I.P. injection 2 × 104 washed *S. typhimurium* 14028s | Bacterial challenge: I.P. injection 2 × 104 washed *S. typhimurium* 14028s |
| 60 | Healthy (n = 10) | Healthy (n = 10) |
| 61 | Healthy (n = 10) | Healthy (n = 0) Sick (n = 10) |
| 62 | Healthy (n = 10) | Healthy (n = 0) Sick (n = 9) Dead (n = 1) |
| 63 | Healthy (n = 10) | Healthy (n = 0) Sick (n = 7) Dead (n = 3) |
| 65 | Healthy (n = 10) | Healthy (n = 0) Sick (n = 6) Dead (n = 4) |
| 68 | Healthy (n = 10) | Healthy (n = 0) Sick (n = 4) Dead (n = 6) |
| 69 | Healthy (n = 10) | Healthy (n = 0) Sick (n = 3) Dead (n = 7) |
| 74 | Healthy (n = 10) | Healthy (n = 0) Sick (n = 2) Dead (n = 8) |
| 76 | Healthy (n = 10) | Healthy (n = 0) Sick (n = 2) Dead (n = 8) |
| 80 | Healthy (n = 10) | Healthy (n = 0) Sick (n = 1) Dead (n = 9) |

To summarize the results of Trial No. 3, ten male mice were vaccinated as indicated above and challenged with 2×10$^4$ washed *S. typhimurium*, strain 14028s. Ten male controls were also challenged with the same number of bacteria. The controls started to become sick on day two of the challenge and began dying on day three. The control mice became very sick, resulting in 9/10 deaths over a three week period. The vaccinated mice never exhibited any sign of illness at any point during the trial. All vaccinated mice, except one mouse in trial 2, continue to thrive and have not shown any signs of bacterial illness.

Discussion of Results

An experimental vaccine was created using the extracellular proteins from a virulent strain of *Salmonella typhimurium*. CD-1 mice were immunized and later challenged with varying doses of the virulent *S. typhimurium*. In all trials, with one exception as explained on Trial No. 2, Day 45, the vaccinated mice exhibited no signs of illness from the infection. However, all of the controls became very sick with numerous deaths occurring, showing that the composition of the present invention is effective at providing protection against disease.

The mechanism of protection is unknown, as the role of bacterial extracellular proteins in facilitating the infectious process in host animals is not known. Further, there is no effective bacterial vaccine constructed with at least one or more extracellular proteins. The results provided by the present invention suggest that an effective immune response was elicited by at least one extracellular protein(s) in the vaccine composition of the present invention.

The mouse model described in the present examples was a model for human typhoid fever, which is an intracellular infection and one that principally relies on a cell-mediated immune response for resistance. One, however, would expect that, upon vaccination with a protein-based immunogenic composition, a humoral, i.e., antibody, response would be the primary response and not a cell-mediated response. Nevertheless, one interpretation of the results obtained here may be that the antibodies produced against the infection specifically interfered/interacted with at least one extracellular protein(s); thus, facilitating cell-mediated immunity. Another interpretation of the results is that the antibodies interfere with the uptake of Iron, which is an essential nutrient for bacterial enzyme activity, such as iron reductase. Still another interpretation is that the immunity observed here involves a synergistic combination of the above-identified biological mechanisms.

The above results demonstrate that an effective vaccine was developed using extracellular proteins from a virulent strain of *S. typhimurium*. However, the present invention was also evaluated using the avirulent *S. typhimurium* strain LT2. The organism was grown and the proteins harvested at an absorbance (660 nm)=0.6, passed over the affinity resin to remove trace amounts of LPS and concentrated. The protein concentration was 14.7 μg/ml resulting in 2.9 μg protein per 200 μl i.p vaccination. There were three vaccinations given to CD-1 mice over a four week period. Five vaccinated mice were then given a lethal dose of virulent *S. typhimurium* strain 14028s, along with five controls. The controls died within 2-5 days. The LT2 vaccinated mice did not show any signs of illness over a four week period and were euthanized at this time. This experiment demonstrates that the composition prepared according to the present invention using extracellular proteins produced by *S. typhimurium* LT2, an avirulent strain, afforded the same protection as that of the composition prepared according to the present invention using the extracellular proteins of virulent *S. typhimurium* 14028s.

These results using both a virulent and an avirulent *Salmonella typhimurium* composition demonstrate that a vaccine produced by using extracellular proteins provided significant protection against a lethal *S. typhimurium* challenge. The composition and method of making and using it, as provided by the present invention, are also effective using a variety of microorganisms. For instance, *Pseudomonas aeurginosa* PAO1, a Gram-negative rod, was grown in M9 media as previously described. Prior work by the inventors (Vartivarian et al. (1999) *Arch. Biochem. Biophys.* 364:75-82; Cowart (2002) *Arch. Biochem. Biophys.* 400:273-281) determined that *P. aeurginosa* PAO1 produced secondary metabolites. As a result, the cultures were harvested between 0.6 and 0.7 absorbant units, 660 nm. However, during concentration of the extracellular proteins a thick, viscous material appeared much like the LPS when concentrating supernatant fluids from *S. typhimurium*.

It was determined that the viscous material was alginate (Linker et al. (1964) *J. Biol. Chem.* 241:3845-3851) and that it could be precipitated by calcium ions. The determination was made that 0.30 M $CaCl_2$ would precipitate essentially all of the alginate produced by *P. aeurginosa* that was harvested at an absorbance (660 nm) between 0.6 and 0.7. The precipitated alginate was centrifuged leaving a clear fluid that was then concentrated to produce the vaccine. The vaccine proteins were dialyzed with PBS in the stirred-cell concentrator containing a 10,000 mw cut off membrane to remove any excess calcium ions, the fluid filter sterilized using a 0.22 μm PVDF filter into sterile vaccine vials and stored at −20 C. Male CD-1 mice were vaccinated i.p. three times with the *P. aeurginosa* PAO1 vaccine, with a protein concentration of 2.8 μg/ml, over a 14 day period for a total protein concentration of 1.12 µg. The $LD_{50}$ of *P. aeurginosa* PAO1 was determined to be $1.4\times10^8$ cells ip. Four male CD-1 vaccinated mice were challenged with $5\times10^8$ cells/0.2 ml ip, along with five unvaccinated mice as controls. Other controls, which will be explained in detail in a later section, consisted of one each of a MRSA, *Listeria*, *Vibrio*, and *Salmonella* LT2 vaccinated mouse. All control mice died within ~12 hours. None of the vaccinated mice showed any signs of illness and were euthanized two weeks later. These results are essentially the same as were obtained with the *S. typhimurium* and gave complete protection against a lethal challenge with *P. aeurginosa* PAO1.

*Staphylococcus aureus* strain FPR3757, a methicillin resistant *Staphylococcus aureus*, or MRSA was obtained for vaccine studies. This Gram-positive cocci was grown in a defined medium that was developed in this laboratory. It consisted of M9 media that was supplemented with MEM nonessential amino acids (Gibco product no. 11140), MEM essential amino acids (Gibco product no. 11130), and MEM vitamin solution (Gibco product no. 11120). The modified M9 medium proved to be an excellent medium for the growth of *S. aureus*. A vaccine was prepared by growing the MRSA to mid-exponential phase and harvesting the cells. The supernatant fluid was filtered through a 0.45 µm PVDF filter and then concentrated using a stirred-cell concentrator containing a 10,000 mw cutoff membrane at 4° C. The vaccine preparation was then washed with sterile PBS and brought to a final volume, filter sterilized and stored at −20° C. in sterile vaccine containers. The protein concentration was measured at 32.4 µg/ml. Male CD-1 mice were three times vaccinated with 0.2 ml of the vaccine over a five week period. Attempts were made to determine the lethal dose of the MRSA strain in CD-1 mice but the lethal cell number was deemed as too high to function as a mouse infectious model. A virulent *Staphylococcus aureus*, strain UCL, was obtained locally from United Clinical Laboratory and it was determined that $5\times10^{10}$ cells ip would consistently give a lethal outcome in nonvaccinated mice. There were six MRSA vaccinated mice that were challenged with $5\times10^{10}$ cells ip of *S. aureus*, strain UCL. Four of the mice died and two survived. There were five controls and all died except one *Listeria monocytogenes* vaccinated mouse. The cross protection of these vaccines will be discussed below.

These results indicate that the MRSA vaccine conferred a partial protection occurred as was initially described above where it is stated, ""Protection" or "protective immunity" refers to the ability of the serum antibodies, or T cell response, or both, induced during immunization to protect (partially or totally) against disease or death caused by an infectious agent. That is, a mammal immunized by the vaccines of the invention will experience limited growth and spread of an infectious microorganism."

The results also suggest that a vaccine prepared using the Gram-positive rod *Listeria monocytogenes*, using the method of the present invention, as described below, also protects against a lethal *S. aureus* infection. One issue with this challenge is that mice appear to be inherently resistant to *S. aureus*. This challenge utilized $5\times10^{10}$ washed cells administered i.p., which is 50 billion cells. It is suggested that this number of cells complicates the challenge in that secondary effects likely occur which may influence the outcome of the infection. To further explore the partial protection of the MRSA to a *Staph aureus* challenge another mouse strain, other animal, or an in vitro model must be identified that will require far less of a challenge dose.

*Listeria monocytogenes*, strain EGD, a small Gram-positive rod was grown in a defined media developed in this laboratory. Here, M9 medium was supplemented with MEM essential amino acids (Gibco product 11130), the amino acids cysteine and glutamine, and the vitamins and growth factors riboflavin, biotin, thiamine, and thioctic acid. This resulted in a medium that supported the growth of this organism. *L. monocytogenes*, strain EGD, was grown to mid-exponential phase and the culture supernatant fluid was harvested by centrifugation. The fluid was filtered through a 0.22 µm PVDF filter and then concentrated using a stirred-cell concentrator with a 10,000 mw cutoff membrane. The fluids were dialyzed by adding PBS and then brought to a suitable volume, filter sterilized and stored in sterile vaccine vials at −20° C. The protein concentration of the vaccine was 29.3 µg/ml.

A determination of the virulence of strain EGD was attempted but the numbers of organisms required for a lethal infection were higher than the inventor had obtained in prior research, so virulent strain 10403s was obtained. The $LD_{50}$ of this strain in male CD-1 mice was determined to be $1.6\times10^4$ organisms administered iv through the tail vein using a 30 ga needle in a volume of 0.05 ml. The mice were anesthetized with ether prior to the iv injection. Male CD-1 mice were vaccinated by administering 0.2 ml of the vaccine i.p. over a 2½ month period. Five vaccinated mice were then challenged with $1.6\times10^5$ organisms administered iv, which represents a 10-fold $LD_{50}$, lethal challenge. There were four unvaccinated controls, along with one each of the following vaccinated mice: MRSA, LT2, *Vibrio parahaemolyticus*, and *Pseudomonas aeruginosa*. The unvaccinated controls died five days after challenge, along with the MRSA vaccinated mouse. At a later date a MRSA vaccinated mouse was challenged with this same challenge dose and the MRSA vaccinated mouse lived. One of the *Listeria* vaccinated mice died.

*Listeria monocytogenes* is classified as an intracellular bacterial pathogen (Mili et al. (1964) *J. Exp. Med.* 120:93-103). Once the organism gains entrance into host tissues it is either phagocytosized, where it can survive in phagocytic cells such as macrophages, or it invades certain host tissues. Thus, protection against a *Listeria* infection is typically thought of as mediated by cell-mediated immunity where antibodies are not involved. In fact, antibodies to *Listeria* have not been found to be effective in protecting against this infectious agent. An explanation as to how and why the *Listeria* vaccine demonstrates protection, along with similarly prepared vaccines from Gram-positive and Gram-negative organisms, is not readily apparent. It is likely specific proteins or enzymes that perform essential functions involved in nutrient procurement or tissue interactions were blocked by the antibodies induced by the vaccine. This apparently resulted in the cells being unable to acquire an essential nutrient, such as iron, or being unable to invade host cells. The fact that other vaccines also resulted in protection to a *Listeria* infection suggests that these proteins or enzymes have similar functions in other organisms, and have common domains that immunologically cross react.

*Vibrio parahaemolyticus*, strain RIMD 2210633 was grown in M9 medium that contained 1.0% additional NaCl, at 37° C. and 200 rpm. The organism was harvested at mid-exponential phase and the supernatant fluids were collected. They were filtered through a 0.22 µm PVDF filter and passed through the affinity resin to remove any LPS. The supernatant fluid was then concentrated on a stirred-cell concentrator containing a 10,000 mw cutoff membrane. The concentrated proteins were dialyzed using PBS, taken to a final concentration, filter sterilized using a 0.22 µm PVDF filter, and stored at −20° C. in vaccine vials. The protein concentration of the *V. parahaemolyticus* vaccine was 16.1 µg/ml. Male CD-1 mice were vaccinated i.p. with 200 µl vaccine three times over a three week period. The $LD_{50}$ of *V. parahaemolyticus* administered i.p. in male CD-1 mice was determined to be $1\times10^8$ cells. It was determined that a 10-fold challenge with *V. parahaemolyticus* resulted in a particularly rapid infection. It was decided to use the lowest dose of organism, $6\times10^8$ organisms administered in a volume of 0.2 ml i.p., that gave 100% lethality. Here five *V. parahaemolyticus* vaccinated mice and three non vaccinated mice were challenged with this dosage. Also included as controls were one each of the following vaccinated mice: *Listeria, Salmonella* LT2, MRSA, and *Pseudomonas*.

Typically, mice are challenged and evaluated in eighteen to twenty hours. However, in the present example, mice started dying at approximately four hours after challenge, with all mice dying within eight hours. The rapid progression of the infection exceeded the ability of the immune system to respond. An assessment and refinement of this experiment has not yet been conducted. The data reported above from other experiments suggests that positive results could be achieved by using an appropriate mouse model where the infection did not progress as rapidly as it did in this case. The *V. parahaemolyticus* vaccine did result in immune protection from challenges by other organisms, and is reported in the next section.

During the course of these experimental challenges mice that were vaccinated with vaccines from the other organisms were included with the non vaccinated controls. There was no immunological basis for including these vaccinated mice with the controls, and in most cases there was just one vaccinated mouse included. However, a pattern soon began to emerge that vaccinated mice were protected against lethal challenges from other unrelated organisms. It is believed that these ancillary control experiments serve to further establish the significance of the extracellular location of these bacterial proteins used in preparing these vaccines. In that cross reactivities were noted these will likely serve to give insight into the specific proteins, or enzymes, involved in conferring immunity. These cross reactions will likely enable the mechanism of the broad spectrum of these immunological protections to be determined some cases, however, the *Vibro* vaccine protected against infection by unrelated organisms.

Based on these results the present invention surprisingly and unexpectedly shows that the antibodies produced by the mice during vaccination, interfere with the function of one or more extracellular proteins, which are pertinent to pathogenesis. These extracellular proteins could be involved with bacterial adherence, colonization, invasion of host tissues, iron uptake or uptake of other nutrients from the host tissues. If antibodies would preclude extracellular proteins from facilitating the colonizing of tissues, then this would prevent the microorganisms from tissue attachment and phagocytic cells would then clear the bacterial cells. If the antibodies were to prevent the extracellular iron reductase from operating, this would prevent iron from being taken up by the bacteria cells and would preclude growth. This would also allow the clearing of the bacteria cells with little or no growth by the challenge pathogen.

Experimental vaccines were created using the extracellular proteins from the following five genera of bacteria: *Salmonella typhimurium*, virulent strain 14028s, and later LT2, an avirulent strain, which also proved to provide complete protection against a 10-fold $LD_{50}$ lethal challenge, Gram-negative rods; *Staphyloccus aureus*, strain FRP3757, a Gram-positive cocci; *Listeria monocytogenes*, strain EGD, a Gram-positive rod; *Pseudomonas aeurginosa*, strain PAO1, a Gram-negative rod; and *Vibrio parahaemolyticus*, strain RIMD 2210633, a Gram-negative rod and a marine organism. CD-1 mice were immunized with the vaccines prepared from these organisms and later challenged with lethal doses of the organism from which the vaccine was prepared.

During all of the vaccinations, no illnesses were observed due to the administration of the vaccines themselves. The *P. aeurginosa* and *S. typhimurium* vaccines resulted in complete protection from lethal challenge where the challenged animals did not exhibit any signs of illness throughout the trail, while the unvaccinated controls succumbed to the infection. In other cases there were partial protections. The *L. monocytogenes* and *S. aureus* vaccines offered partial protection, which is significant and suggests that optimizations can occur

TABLE 5

Results of Challenge.

|  | Salmonella Challenge | Pseudomonas Challenge | Staphylococcus Challenge | Listeria Challenge | Vibrio Challenge |
|---|---|---|---|---|---|
| Salmonella Vaccine | Complete Protection | No Protection | No Protection | Protection | Unable to Determine |
| Pseudomonas Vaccine | Not Carried Out | Complete Protection | No Protection | Protection | Unable to Determine |
| MRSA Vaccine | Complete Protection | No Protection | Partial Protection | Partial Protection | Unable to Determine |
| Listeria Vaccine | Partial Protection | No Protection | Partial Protection | Protection | Unable to Determine |
| Vibrio Vaccine | Not Carried Out | No Protection | Partial Protection | Protection | Unable to Determine |

By Complete Protection, it us meant that there was no indication of illness upon lethal challenge. By Protection, it is meant that the animals were protected against lethal challenge and may have shown slight signs of illness. By Partial Protection, it is meant that one, or more, vaccinated animals may have died, but others survived the challenge. Relating to the *Vibrio* Challenge, these was not successful in that the infection progress at an extremely rapid rate, where all animals succumbed to the infection by 8 hours. Thus, the organism grew faster than the immune system could respond. In that will even more protection from infection by these organisms. In the case of challenge by *V. parahaemolyticus* the infection progressed at an extremely rapid rate resulting in deaths of all vaccinated mice and controls. This was a result of growth of the organism exceeding the capacity of the immune system to protect. The fact that cross protections were noted to occur suggests that there is/are extracellular proteins or enzymes that are necessary to either growth or pathogenesis that are common to numerous species and that these proteins or enzymes share common domains that are structurally similar. This would account for the immunological cross reactivities. The mechanism of protection is unknown, as there have been no scientific studies on the role of bacterial extracellular proteins in facilitating the infectious process in host animals. The results here suggest that an effective immune response was elicited by the extracellular proteins in the vaccine. Based on the results, it is believed that antibodies interfered with intracellular pathogenesis.

It is believed all microorganisms produce extracellular proteins and enzymes. While some of these proteins function as toxins, the role of these proteins in facilitating interactions with host tissues and their role in the pathogenic process are unknown. A hypothesis presented here is that extracellular microbial proteins play a critical role in facilitating the interaction of Gram-negative or Gram-positive pathogenic organisms with host tissues. This could involve colonization, invasion, procurement of iron or other nutrients, and other functions yet to be determined. Therefore, we claim the process of preparing a vaccine from extracellular protein components for all Gram-negative and Gram-positive microbial pathogens.

Figure 3:
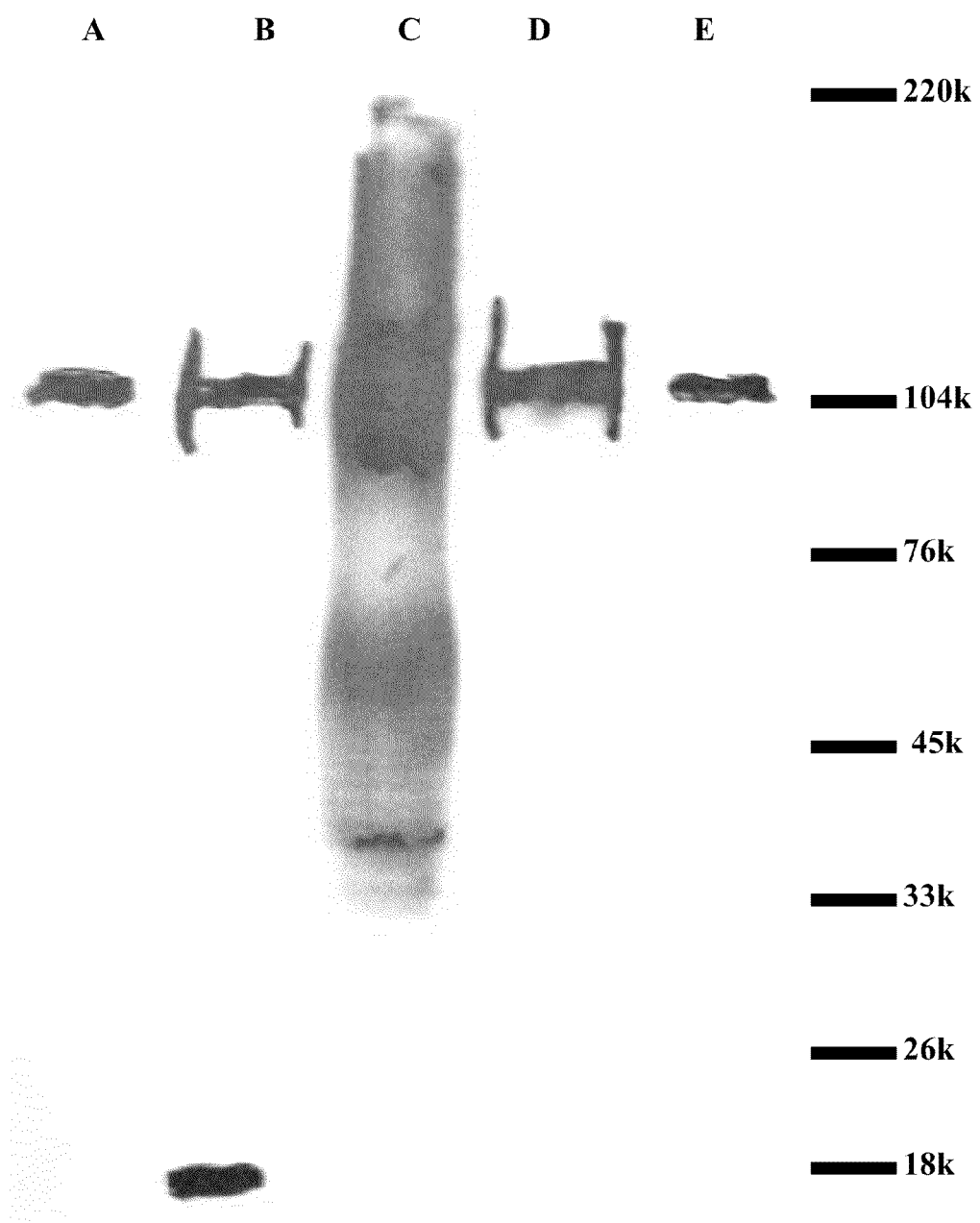
FIG. 3 is a Western Blot analysis showing the cross-reactivity of five different bacterial strains developed against *Salmonella typhimurium*, strain LT2, antiserum. The vaccines were prepared using *Pseudomonas aeurginosa* (Lane A), strain PAO1; *Vibrio parahaemolyticus*, strain RIMD 2210633 (Lane B); *Salmonella typhimurium*, strain LT2 (Lane C); *Staphylococcus aureus*, strain FPR3757 (Lane D) and *Listeria monocytogenes*, strain EGD (Lane E) and were electrophoresed using the standard SDS-PAGE protocol. Prestained molecular weight markers were visible on the blot prior to processing. The proteins were then transferred to a nitrocellulose membrane according to a standard, wet Western blot technique. The nitrocellulose membrane was blocked with 5% nonfat dry milk in PBS containing 0.05% Tween 20. The blot was then incubated with a polyclonal IgG that had been isolated from CD-1 mice that had been vaccinated with *Salmonella typhimurium*, strain LT2. The isolation of the mouse antibodies was accomplished by affinity chromatography using an agarose resin to which were attached two engineered proteins; Protein A and Protein G (Pierce/Thermo Fisher). These proteins have a high affinity for mouse IgG and are suitable for affinity isolation of this antibody from mouse serum. The anti-Salmonella antibodies were collected and diluted 1:5000 and incubated with the blocked nitrocellulose blot for 1 hour at room temperature while gently shaking. The blot was washed in PBS/Tween 20 buffer and then incubated with a goat anti-mouse IgG that was tagged with horse radish peroxidase (Pierce/Thermo Fisher), with incubation for 1 hour at room temperature while gently shaking. The blot was then washed with the PBS/Tween 20 buffer and the horse radish peroxidase activated (Pierce/Thermo Fisher). The blots were used to expose X-ray film at various time intervals. Some signals were very strong at a 10 second exposure, others at 1 minutes, and yet others at 10 minutes.

To address this observation that mice vaccinated with one vaccine would be completely resistant to a challenge by an organism unrelated to the vaccine, an experiment was set up to identify if any immunological cross reactions were occurring. The technique used is known as a Western blot analysis. Here, all five vaccine proteins were electrophoresed by standard SDS-PAGE. The proteins were then transferred to a nitrocellulose membrane. After blocking nonreactive protein binding sites the membrane was incubated with mouse antibodies produced in response to the *Salmonella* vaccine. The membrane was washed and then incubated with goat antimouse IgG that had been coupled with horse radish peroxidase (HRP). The HRP was developed so as to produce a highly intense chemiluminescense and the membrane was then used to expose X-ray film. In FIG. 3, there is a single protein band with a molecular weight between about 90 and about 115 kDa. The interpretation is that the anti-Salmonella antibodies cross reacted with this particular protein, and that this protein serves an essential function(s) for the survival of the organisms. This then explains why there is cross protections with the vaccinated mice. FIG. 3 is a composite figure illustrating the three different exposure times, i.e., 10 seconds, 60 seconds, and 20 minutes, required to visualize all of the bands. It was noted in the vaccine trials that *Pseudomonas*-vaccinated mice did not protect against any of the other microbial pathogens, and 20 minutes were required to visualize the band in the *Pseudomonas* vaccine. This is interpreted as indicating that the immunological cross reactivity in *Pseudomonas* is less than the immunological cross reactivity of proteins in the other vaccines, thus the immunological protection was less. Regardless, the protein is present and all of the *Pseudomonas* vaccine mice were completely protected against lethal challenge by *Pseudomonas*. These results suggest that it is possible to engineer a single protein vaccine that would theoretically protect against all pathogens that produce this protein.

Therapeutic Applications

Possible therapeutic applications include the vaccination of infected patients who are not responding to antibiotics. By administering the vaccine, it is possible that large amounts of antibodies would be produced by the host that would target the extracellular protein(s) essential to the growth of the microorganism. It is also possible that the essential protein(s) of interest, once identified and crystallized, could be modeled; so as to rationally design and synthesize a small ligand inhibitor capable of binding to the protein of interest. This binding would result in a conformational change that would reduce or preclude activity that would lead to pathogenesis. Such a small ligand inhibitor could be useful in treating antibiotic resistant infections.

Although the foregoing invention has been described in some detail by way of illustration and example for purposes of clarity of understanding, it is understood that certain adaptations of the invention are a matter of routine optimization for those skilled in the art and can be implemented without departing from the spirit of the invention or the scope of the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A composition for immunizing a subject against a pathogenic bacteria, the composition comprising a supernatant fluid from growth cultures of *Pseudomonas aeruginosa, Vibrio parahaemolyticus, Salmonella typhimurium, Staphylococcus aureus,* and *Listeria monocytogenes,* wherein when the composition is administered to a subject it confers at least partial protection to the subject from lethal challenge by a pathogenic bacteria comprising at least *Pseudomonas aeruginosa, Vibrio parahaemolyticus, Salmonella typhimurium, Staphylococcus aureus,* and *Listeria monocytogenes.*

2. The composition of claim 1, wherein the composition is free of soluble lipopolysaccharide.

3. The composition of claim 1, wherein the composition comprises extracellular proteins.

4. The composition of claim 3, wherein at least one majorly abundant extracellular protein is in the range of from about 10 kDa to about 200 kDa.

5. The composition of claim 4, wherein the at least one majorly abundant extracellular protein is in the range of from about 20 kDa to about 180 kDa, about 40 kDa to about 160 kDa, about 60 kDa to about 140 kDa, or about 80 kDa to about 120 kDa.

6. The composition of claim 1, wherein the supernatant comprises an extracellular protein in the range of about 90 kDa to about 115 kDa from each growth culture.

7. The composition of claim 1 further comprising at least one of a pharmaceutically-acceptable carrier, an excipient, a wetting agent, an emulsifying agent, a stabilizer, a preservative, a pH buffering agent, a viscosity enhancing additive, and a colorant.

8. The composition of claim 7, wherein the pharmaceutically-acceptable carrier comprises at least one of water, an oil, or a saline.

9. The composition of claim 7, wherein the excipient comprises at least one of starch, glucose, lactose, sucrose, gelatin, malt, rice, flour, chalk, silica gel, sodium stearate, glycerol monostearate, talc, sodium chloride, dried skim milk, glycerol, propylene, glycol, and ethanol.

10. The composition of claim 1, wherein the composition is sterile.

11. The composition of claim 1, wherein the subject is a mammal.

12. The composition of claim 11, wherein the mammal is selected from the group consisting of humans, mice, cows, pigs, horses, cats, and dogs.

13. The composition of claim 1, wherein the subject is a non-mammal.

14. A method for immunizing a subject against a pathogenic bacteria, the method comprising administering to a subject a composition comprising a supernatant fluid from growth cultures of *Pseudomonas aeruginosa, Vibrio parahaemolyticus, Salmonella typhimurium, Staphylococcus aureus*, and *Listeria monocytogenes*, wherein the composition confers at least partial protection to the subject from lethal challenge by a pathogenic bacteria comprising at least *Pseudomonas aeruginosa, Salmonella typhimurium, Staphylococcus aureus*, and *Listeria monocytogenes*.

15. The method of claim 14, wherein the subject is selected from the group consisting of humans, mice, cows, pigs, horses, chickens, cats and dogs.

16. The method of claim 14, wherein the administering step is performed at least one of intramuscularly, intraperitoneally, or intradermally.

17. A method of conferring at least partial immunity against a pathogenic bacteria to a subject, comprising:
(a) culturing *Salmonella typhimurium* and *Pseudomonas aeruginosa* and at least one of *Vibrio parahaemolyticus, Staphylococcus aureus*, and *Listeria monocytogenes* under conditions sufficient to yield supernatant fluid;
(b) isolating supernatant fluid from the cultures to form an immunogenic composition;
(c) sterilizing the immunogenic composition; and
(d) administering an effective amount of the immunogenic composition to a subject;
wherein the immunogenic composition confers at least partial protection to the subject from lethal challenge by a pathogenic bacteria comprising *Pseudomonas aeruginosa, Salmonella typhimurium, Staphylococcus aureus*, and *Listeria monocytogenes*.

18. The method of claim 17, wherein step (a) comprises culturing *Salmonella typhimurium, Pseudomonas aeruginosa*, and *Vibrio parahaemolyticus* under conditions sufficient to yield a supernatant fluid.

19. The method of claim 17 further comprising step (b)(i) removing soluble lipopolysaccharide.

20. The method of claim 17 further comprising step (e) evaluating the subject's antibody population to demonstrate antibodies specific for extracellular proteins from at least *Salmonella typhimurium* and *Pseudomonas aeruginosa* and at least one of *Vibrio parahaemolyticus, Staphylococcus aureus*, and *Listeria monocytogenes*.

* * * * *